US008828916B2

(12) United States Patent
Simard

(10) Patent No.: US 8,828,916 B2
(45) Date of Patent: Sep. 9, 2014

(54) METHOD TO PREPARE NONYLATED DIPHENYLAMINE USING RECYCLE SEQUENTIAL TEMPERATURES

(75) Inventor: Francois Simard, Novato, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 731 days.

(21) Appl. No.: 11/960,834

(22) Filed: Dec. 20, 2007

(65) Prior Publication Data

US 2008/0161216 A1  Jul. 3, 2008

Related U.S. Application Data

(60) Provisional application No. 60/882,284, filed on Dec. 28, 2006.

(51) Int. Cl.
*C10M 133/12* (2006.01)
*C07C 209/68* (2006.01)

(52) U.S. Cl.
CPC ........... *C07C 209/68* (2013.01); *C10N 2230/10* (2013.01); *C10N 2220/021* (2013.01); *C10M 2215/065* (2013.01); *C10M 2215/064* (2013.01); *C10M 133/12* (2013.01)
USPC .......................................... 508/563; 564/409

(58) Field of Classification Search
CPC .................... C10M 133/12; C10M 2215/064; C10M 2215/065; C10M 2215/022; C10M 2215/223; C10M 2215/066; C10M 2215/067; C10M 2215/068; C10M 2215/221; C10M 2215/225; C10M 2215/226; C10M 2215/26; C10M 2215/30; C10M 2215/08; C10M 2215/082; C10M 2215/086; C10M 2215/12; C10M 2215/122; C10M 2215/224; C10M 2215/24; C10M 2215/28; C10M 2217/046; C10M 2217/043; C10M 2217/28; C10M 169/04; C10M 101/02; C10M 107/02; C10M 2223/04; C10M 2207/026; C10M 2207/281; C10M 2207/262; C10M 2207/021; C10M 2207/04; C10M 2207/042; C10M 2207/10; C10M 2207/126; C10M 2207/144; C10M 2207/24; C10M 2207/28; C10M 2207/40; C10M 2219/085; C10M 2219/086; C10M 2219/10; C10M 2219/102; C10M 2219/04; C10M 2201/02; C10M 2201/087; C10M 2201/10; C10N 2230/10; C10N 2230/021; C10N 2230/06; C10N 2230/02; C10N 2230/30; C10N 2230/74; C10N 2230/76; C10N 2210/02; C10N 2210/06; C10N 2210/01; C10N 2240/08; C10N 2240/30; C10N 2240/06; C10N 2240/401; C10N 2240/402; C10N 2240/409; C10N 2240/02; C10N 2240/101; C10N 2240/102; C10N 2220/22; C10N 2220/24; C10N 2220/25; C10N 2220/28; C10N 2220/31; C10N 2220/32; C10N 2220/302; C10N 2220/303; C10N 2220/306; C10N 2220/021; C07C 209/68; C07C 211/55
USPC .................... 508/563; 564/409, 395; 585/323
See application file for complete search history.

(56) References Cited

U.S. PATENT DOCUMENTS

| | | | |
|---|---|---|---|
| 2,943,112 A | 6/1960 | Popoff et al. | |
| 3,496,230 A * | 2/1970 | Kaplan | 564/409 |
| 4,739,121 A | 4/1988 | Shaw | |
| 4,824,601 A | 4/1989 | Franklin | |
| 5,186,852 A | 2/1993 | Ishida et al. | |
| 5,214,211 A | 5/1993 | Kurek et al. | |
| 5,672,752 A | 9/1997 | Lai et al. | |
| 5,734,084 A * | 3/1998 | Zhu | 564/409 |
| 5,750,787 A | 5/1998 | Lai et al. | |
| 5,817,831 A | 10/1998 | Rhubright et al. | |
| 5,986,155 A * | 11/1999 | Burrington et al. | 585/323 |
| 5,997,732 A | 12/1999 | Yenni et al. | |
| 6,204,412 B1 | 3/2001 | Lai | |
| 6,310,154 B1 | 10/2001 | Babcock et al. | |
| 6,315,925 B1 * | 11/2001 | Aebli et al. | 252/401 |
| 6,355,839 B1 | 3/2002 | Onopchenko | |
| 6,376,625 B1 | 4/2002 | Cosman et al. | |
| 6,930,183 B2 | 8/2005 | Duyck et al. | |
| 2004/0211113 A1 | 10/2004 | Duyck et al. | |
| 2006/0276677 A1 * | 12/2006 | Elnagar et al. | 564/395 |

FOREIGN PATENT DOCUMENTS

| | | |
|---|---|---|
| EP | 0 818 432 A1 | 2/1998 |
| GB | 2325929 A * | 12/1998 |
| WO | WO 01/23343 A2 | 4/2001 |
| WO | WO 2006/130498 A | 12/2006 |

OTHER PUBLICATIONS

Burrington, J.D., et al., "Catalytic Isomerization and Dechlorination of Nonenes", Applied Catalysis A: General, 2001, 210, pp. 193-206, Elsevier.
Chitnis, Sandeep R., et al., "Alkylation of Diphenytamine with a-Methylstyrene and Diisobutylene Using Acid-Treated Clay Catalysts", Journal of Catalysis 160, 84-94 (1996) Article No. 0126, Academic Oress, Inc.
Gatto, Vincent J., et al.., "Redesigning Alkylated Diphenylamine Antioxidants for Modern Lubricants", Lubrication Science 2007; 19: 25-40, Wiley & Sons.

(Continued)

*Primary Examiner* — James Goloboy
*Assistant Examiner* — Latosha Hines

(57) ABSTRACT

The present invention relates to a process for preparing nonylated diphenylamines which improves nonene usage by recycling and reusing stripped nonene from an earlier process. The process comprising consecutive recycle of recovered nonene is conducted at a sequential two step temperature reaction, namely a more severe temperature followed by a lower temperature. The product prepared by this process is a useful antioxidant for lubricating oil compositions.

17 Claims, No Drawings

(56) References Cited

OTHER PUBLICATIONS

Burrington, J.D., et al., "Catalytic isomerization and dechlorination of nonenes", Applied Catalysis A: General, 2001, 210, pp. 193-206.

Gatto, V.J. et al., "Redesigning alkylated diphenylamine antioxidants for modern lubricants", Lubrication Science, 2007, 19, pp. 25-40.

Chitnis, S.R., et al., "Alkylation of Diphenylamine with a-Methylstyrene and Diisobutylene Using Acid-Treated Clay Catalysts", Journal of Catalysis, 1996, 160, pp. 84-94.

* cited by examiner

METHOD TO PREPARE NONYLATED DIPHENYLAMINE USING RECYCLE SEQUENTIAL TEMPERATURES

FIELD OF THE INVENTION

The present invention relates to a process for preparing nonylated diphenylamines which improves nonene usage by recycling and reusing stripped unreacted nonene from an earlier process. The process comprises consecutive recycle of recovered nonene is conducted at a sequential two step temperature reaction. The nonene alkylated diphenylamine product mixture is a useful antioxidant when added to a lubricating composition.

BACKGROUND OF THE INVENTION

Alkylated diarylamines, such as alkylated diphenylamine, are well known in the art and function as stabilizers or antioxidants in a wide variety of organic materials, including, among other organic materials, mineral oil derived lubricants and synthetic lubricants. In this application a light colored liquid product (at about 20° C.) having a low concentration of unreacted diphenylamine is desirable for a number of practical reasons.

Alkylation of diarylamines, such as diphenylamine, with olefins in the presence of suitable alkylation catalysts is well known in the art. Typically unreacted diphenylamine when present in objectionable amounts has been removed by high temperature, high vacuum distillation of the crude product. These distillation techniques, made necessary by the high boiling points and thermolabile properties of the products are expensive process steps and lead to further product loss. Other techniques have used to reduce the amount of unreacted diphenylamine; for example methods have directed to using extremely large excess of alkylate in comparison to the diphenylamine, U.S. Pat. No. 5,186,852 (Ishida et al.) exemplifies eight fold excess of alkylate. As is apparent, the use of a large excess of alkylate is not particularly cost effective. Recycling of alkylate has been problematic; the residual alkylating agent has lower reactivity than the starting alkylate partly due to rearrangement products being formed and the alkylation agent can be halogenated by the catalyst in Friedel-Crafts alkylation. Commonly, the unreacted alkylate has been used for other applications such as fuels, however depending upon the halogen content these alternative uses may be limited. U.S. Pat. No. 3,452,056 describes the preparation of a mixture of 80% dinonyldiphenylamine, 15% mono-nonyldiphenylamine and about 2% unreacted diphenylamine using Friedel-Crafts alkylation in the presence of Lewis Acid catalysts wherein $AlCl_3$ and $ZnCl_2$ are mentioned as suitable catalysts. Lewis Acid catalysts are somewhat undesirable, since they may lead to halogenation of the product and due to degree of process water generated in the purification.

In a different approach, commonly employed for preparing isobutylene derived diphenylamines, a more reactive scavenging alkylate is used to further alkylate the unreacted diphenylamine. U.S. Pat. No. 2,943,112 (Popoff et al.) teaches a two step process whereby alkylation of diphenylamine with relatively unreactive olefins, such as secondary alkenes (column 4, line 9-23), is followed by an alkylation reaction with more reactive olefins to scavenge the unreacted diphenylamine. Popoff also teaches the use of acid activated clay as an alkylation reaction catalyst to achieve the desired light color.

Similarly, Franklin, U.S. Pat. No. 4,824,601, (column 1, lines 26-67), teaches the use of acidic clay catalysts to alkylate diphenylamine and further teaches that a light colored, liquid product may be prepared by process comprising reacting the alkylation reactants within certain molar ratios and temperature ranges for a time sufficient to ensure the alkylated product contains less than 25% dialkylated diphenylamine. This low proportion of dialkylated diphenylamine is disclosed as necessary to avoid the formation of crystallized, solid products, which are not advantageous in terms of ease of handling, transportation, storage and incorporation into the substrate to be stabilized. This crystallization issue is a concern when alkylating diphenylamine with diisobutylene and is a lesser concern when employing nonene.

Also in addressing the same problem, namely, preparing an effective antioxidant from diphenylamine and diisobutylene that is liquid at room temperature, Lai in U.S. Pat. Nos. 5,672,752 and 5,750,787, teaches processes for alkylating diphenylamine with linear alpha olefins and diisobutylene in the presence of a clay catalyst. These processes as disclosed, selectively result in a higher proportion of monoalkylated diphenylamine and a lower proportion of unsubstituted diphenylamine and/or disubstituted or polysubstituted diphenylamines. These patents further disclose that to obtain the desired liquid product, the ratio of olefin to diphenylamine in the reaction mixture, together with reaction temperature and time is important to give a product mixture with less than 25% dioctyldiphenylamine, less than 25% unreacted diphenylamine and greater than 50% by weight monooctyldiphenylamine based on the total weight of the diphenylamine and alkylated DPA.

In U.S. Pat. No. 6,204,412 (Lai) Lai discloses yet another method of alkylating diphenylamine to obtain a light colored, liquid product, which comprises a two step method wherein, in the second step, a second olefin is added to the reaction mixture containing diphenylamine and diisobutylene (and/or an alpha-olefin of the disclosed formula) to scavenge or reduce the amount of unreacted diphenylamine in the product As with U.S. Pat. Nos. 5,672,752 and 5,750,787, specific mole ratio ranges, reaction temperatures and reaction times are disclosed as important to obtain the desired alkylated diphenylamine that is liquid at room temperature.

U.S. Pat. No. 6,315,925 (Aebli et al.) discloses alkylating diphenylamine with excess nonene in the presence of an acid earth and in the absence of a free protonic acid. The particular composition is defined by an area percent of a gas chromatograph, more particularly defined by having not more than 3.5% by area trinonyldiphenylamine.

SUMMARY OF THE INVENTION

The present invention relates to the preparation of alkylated diphenylamine antioxidant compositions using nonene as the alkylating reagent, recycling recovered residual nonene and employing two distinct reaction temperatures. Advantageously, the nonene usage (for alkylation of diphenylamine) is improved and conversions approach eighty percent.

Accordingly, the present invention is directed to a process for preparing an alkylated diphenylamine using consecutive recycle of recovered nonene, said process comprising:

a) recovering residual nonene from an acid clay catalyzed alkylation reaction of nonene with diphenylamine;

b) charging diphenylamine and recovered residual nonene from step a) with nonene or isometric nonene to a reactor with an acid clay catalyst;

c) heating the reactor to a first temperature of from about 175° C. to about 200° C. in the presence of acid clay catalyst under reactive conditions for a suitable period of time to alkylate a majority of charged diphenylamine;

d) reducing the reaction temperature to a second temperature of from about 140° C. to about 160° C. for a suitable period of time such that the total composition contains less than about 1 wt % of unreacted diphenylamine;

e) repeating steps a) through d).

The process of the present invention leads to an alkylated diphenylamine product which is liquid at room temperature and atmospheric pressure. The consecutive recycle of nonene to the reactor can be sequential and step e) can be repeated a plurality of times, thus for example steps a) through d) can be repeated for multiple sequences. Preferably, step e) is repeated three or more times. Typically, the process is terminated when the unreacted diphenylamine in step d) is greater than about 1 wt % or the time period to achieve the results has doubled from the initial run.

Employing recycled unreacted nonene improves the overall usage and conversion of nonene and minimizes reagent waste. However, the recycle also adds some difficulty since the recovered nonene may include isomerized and degradation products which will react differently than fresh nonene in the alkylation reaction. Preferably the nonene is added in a molar excess to the diphenylamine, such as 4 to 6 times excess. In this instance, the total recovered residual nonene preferably is from about 25 to about 50 mole percent of the total nonene charged to the reactor, more preferably from about 25 to about 60 mole percent of the total nonene charged to the reactor, and even more preferably 40 to about 60 mole percent of the total nonene charged to the reactor.

The process uses a sequential temperature for the alkylation reaction. The first temperature is selected to be more severe, preferably the first temperature is from 175° C. to about 200° C. more preferably from about 180° C. to 195° C., the second temperature is less severe and preferably the second temperature is from about 140° C. to about 160° C. more preferably from about 145° C. to 155° C.

In addition to diphenylamine, other aromatic amines are subject to alkylation by the disclosed process. Such other aromatic amines include, for example: N-phenyl-1-naphthylamine, N-phenyl-2-naphthylamine, p,p'-phenylenediamine, phenothiazine, phenoxazine, p-amino-diphenylamine, p-methylamino-diphenylamine and p-isopropylamino-diphenylamine.

In another aspect the present invention is directed to a product prepared by the process comprising:

a) recovering residual nonene from an acid clay catalyzed alkylation reaction of nonene with diphenylamine;

b) charging diphenylamine and recovered residual nonene from step a) with nonene or isomeric nonene to a reactor with an acid clay catalyst;

c) heating the reactor to a first temperature of from about 175° C. to about 200° C. in the presence of acid clay catalyst under reactive conditions for a suitable period of time to alkylate a majority of charged diphenylamine;

d) reducing the reaction temperature to a second temperature of from about 140° C. to about 160° C. for a suitable period of time such that the total composition contains less than about 1 wt % of unreacted diphenylamine;

e) recovering alkylated diphenylamine reaction products from the reactor; and f) repeating steps a) through e).

Particularly preferred alkylated diphenylamine reaction products are characterized by having from about 15 to about 30 weight % for the monoalkylate; from about 65 to about 75 weight. % for the dialkylate; and from about 5 to about 12 weight % for the trialkylate. More preferably, the alkylated, diphenylamine product is characterized by having from about 15 to about 25 weight % for the mononoyldiphenylamine; from about 65 to about 75 weight % for the dinonyldiphenylamine; and from greater than about 7 to about 10 weight % for the trinonyldiphenylamine; with trinonyldiphenylamine greater than about 8 weight % particularly preferred. It has been predicted that compositions containing this elevated amount of dinonyldiphenylamine and more particularly trinonyldiphenylamine would be less volatile, more stable and be well suited as an antioxidant in this class of lubricating compositions.

DETAILED DESCRIPTION OF THE INVENTION

As noted above, the present invention provides a liquid alkylated diphenylamine, which is an effective antioxidant, by a process comprising alkylating diphenylamine with a nonene oligomer under suitable alkylation reaction conditions in the presence of a suitable alkylation catalyst. Generally, the nonene oligomer includes nonene and isomeric nonenes, including α-olefins and tertiary olefins. Preferably, the nonene is derived by polymerization of propylene and is commonly referred to propylene trimer. Typically, the propylene trimer is a product of propylene polymerization with a phosphate (phosphoric acid based) catalyst. As such, the product contains a majority of propylene trimer, typically having a mass content greater than about 85%, preferably about 90 to 97%, and more preferably having about 95% or greater. The propylene trimer has a minimum amount of $C_8$ olefins and lower and a minimum amount of $C_{10}$ olefins and higher, typically less than 5% mass content of each, more preferably less than 3% each. A suitable product may have a $C_8$ olefins and lower mass content maximum of 2.0% and a $C_{10}$ olefin and higher mass content maximum of 3.0%. The alkylation of diphenylamine reactant using propylene trimer affords nonylated diphenylamine compositions and a minority of other reaction products, wherein nonylated diphenylamine refers to all diphenylamines alkylated with any nonene isomer. Commercial sources of suitable propylene trimer are for example Sunoco Inc., Philadelphia, Pa. and ExxonMobil Chemicals, Houston, Tex.

Nonene employed in the process is used in a molar excess based upon diphenylamine charged to the reactor. Preferably the total nonene is charged in a about a 3- to 6-molar excess based upon the moles of diphenylamine charged, more preferably about a 4-fold molar excess.

The use of clay as catalyst in the alkylation of diphenylamine is disclosed in U.S. Pat. No. 3,452,056, which describes the alkylation of diphenylamine with alpha-methylstyrene and related olefins with clay as the catalyst. In U.S. Pat. No. 2,943,112 and other prior art, clay is described as having several advantages including, for example: (1) as having the advantage of giving lighter colored product, (2) ease of removal by filtration after the reaction and (3) a lower degree of yellow color in the alkylated product. As a catalyst, clay and other Lewis Acids, such as $AlCl_3$ or $BF_3$ are generally taught as being interchangeable. (See, U.S. Pat. Nos. 3,452,056 and 5,672,752 at col. 3, ln. 3-6 and col. 1, ln. 33-41, respectively). Due to the consecutive sequential recycle of nonene in the present invention, Lewis Acids are not preferred alkylation catalysts since residual halogen content in the alkylate is undesirable. Preferably the halogen content of the recycled components are less than 1.0 weight percent, more preferably less than 0.05 weight % and even more preferably the reaction is substantially free of halogen content.

Suitable clay catalysts are disclosed in U.S. Pat. Nos. 5,672,752; 5,750,787 and 6,204,412, the disclosures of which are incorporated herein by reference in their entirety. Commercially available clay catalysts, including; Filtrol™ and Retrol™ available from BASF, Fulcat™ 14, Fulmont™ 700C, Fulmont™ 237, and Fulcat™ 22B available from Rockwood Additives Comp); and Katalysator™ K10 available from Sud-Chemie. These clays may include acid activated or acid leached clays. Suitable acid treated clays available from BASF include: "F-1", "F-2", "F-6", "F-13", "F-20X", "F-22", "F-24", "F-105", and "F-160"; wherein "F-20X" and "F-24" are particularly preferred. The clay catalysts may contain some water as received. Removal of the water prior to use results in a lighter colored reaction product and may maximize the catalyst acidity and activity toward alkylation. The freely associated water may be removed by various techniques including thermal treatment, reduced pressure treatment, dry atmosphere treatment such as nitrogen or air, or a combination thereof. The freely associated water removed from the solid acid catalyst may have been derived from water (physisorbed water) or hydroxyl groups (chemisorbed water) associated with the catalyst. By removal of substantially all freely-associated water is meant removing essentially all physisorbed water and removing at least a majority of chemisorbed water. Therefore, it is desirable to use clay with low water content or remove the water by heating the clay with a nitrogen sweep or with vacuum stripping. Likewise, the feed streams should include less than about 500 ppm water, preferably less than 200 ppm water, more preferably less than 100 ppm water and most preferably less than about 50 ppm water. Acid activated clays are preferred.

The preferred clays are aluminosilicates. Aluminosilicate clays are typically compounds of aluminum silicate with other metal oxides such as, for example, aluminum oxide and silicon dioxide, or other radicals. The structure of such clays, are commonly hexagonal closed pack array or oxygen ions with aluminum ions occupying approximately two thirds of the octahedral holes in the ordered array. The aluminum III cations of the clay catalysts are typically bonded in an octahedral arrangement to oxygen anions. Repetition of these $AlO_6$ units in two dimensions forms an octahedral layer. Likewise a tetrahedral layer is formed from $SiO_4$ silicate units. Clays are classified according to the relative number of tetrahedral and octahedral layers. Activated clays are commonly prepared by the acid activation of sub-bentonites or bentonites and may include montmorillonite. Montmorillonite clays, have been used in organic chemical applications, have a octahedral layer sandwiched between two tetrahedral layers. Particularly preferred acid activated montmorillonite clays include those available from BASF such as F-24 and more preferably powder grade montmorillonite clay sold as F-20 and F-20X. The acid clays used in the process can be removed from the reaction mixture by filtration, centrifugation or decanting. In practice the acid clays are employed in an amount from 5.0 to 20.0 weight % by weight of diphenylamine and preferably from about 10.0 to 20.0% by weight. Preferred clay catalyst typically have a bulk density from about 400-700 grams/liter; a total acidity of from 5 to about 20 mg KOH/g and a surface area of from 150 to about 350 $m^2/g$ (BET method). The clay catalyst can be a coarse product, such as 10/20 mesh, preferably a more granular product at about 10/60 mesh, and more preferably a powder product for example having an average particle size about 30 microns.

The clay catalysts employed in the present invention offer several advantages over Lewis Acids (e.g. $AlCl_3$, $AlBr_3$, $BF_3$, complexes of $BF_3$, $TiCl_4$, and other which are traditionally used for Friedel-Crafts reactions). Many of these advantages are a result of the acid sites being an integral part of the solid catalysts thus limiting contamination. As a result, the clay catalysts due not impart color to the product due to catalyst residues. Generally, the clay catalysts can be regenerated and recycled to thereby minimize waste disposal of spent catalysts. In contrast, Lewis Acids are generally single use catalysts and typically generate corrosive liquids upon separation.

Although solvents have been used in alkylation reactions, it is preferred in this disclosure to alkylate with minimal solvent or no solvent at all. If a solvent is used, suitable solvents include for example mineral spirits, toluene, xylene, or aromatic solvents such as Aromatic and Sovesso™ fluids from Exxon Chemical Company or Shellsol™ fluids from Shell Chemical Company.

The unreacted olefins may be removed from the reaction product by distillation. Similarly, the unreacted diphenylamine may be removed by process such as fractional distillation or vacuum distillation if necessary. Typically, subsequent removal of the unreacted diphenylamine is unnecessary since due to the process disclosed in the present invention, the alkylated diphenylamine product beneficially has a low residual amount of unreacted diphenylamine. The amount of diphenylamine in the product is desirably less than about 1.0 weight percent in the final product and preferably less than about 0.8 weight percent in the final product. (The clay can be removed by filtration or other known separation methods).

The alkylation reaction can be carried out in an autoclave if high pressures due to the vapor pressure of the olefin are anticipated or for other reasons. The pressure used for the reaction is primarily controlled by the olefin used and the reaction temperature. As the product is always liquid, the reactants and products may be pumped into and out of the reactor. For purposes of this invention the preferred catalyst was determined to be BASF F-24 acid-activated clay (formerly Filtrol's Retrol clays).

The reaction temperature for the alkylation reaction is a sequential temperature having different temperature ranges. The first temperature is in range of about 175° C. to about 200° C., preferably in the range of about 180° C. to about 195° C., and more preferably in the range of about 180° C. to about 190° C. The first reaction temperature is relatively severe, due in part to the degree of recycled nonene added to the process. The unreacted stripped nonene recycled from a previous batch is typically the least reactive part of the fresh nonene originally reacted. The recycled nonene may contain isomerized species or degradation products which differ in their degree of reactivity in the alkylation reaction. It has been discovered that mixed recycled nonene/nonene mixture, initially requires more aggressive reaction conditions. Typically the recycled nonene is charged to the reactor and fresh nonene is added to the desired charge mole ratio and the reactor is heated. Preferably, at least 25 mole percent to about 60 mole percent of the nonene charged to the reactor is recovered residual nonene, more preferably at least 35 mole percent and even more preferably 40 mole percent to about 60 mole percent of the nonene charged to the reactor is residual nonene from an earlier alkylation reaction. The first temperature range is maintained for a suitable period of time so that the majority of the charged diphenylamine is alkylated. Thereafter, the reaction temperature is reduced to a second temperature in range of about 140° C. to about 160° C., preferably in the range of about 145° C. to about 155° C., and more preferably in the range of about 150° C. to about 155° C. The second temperature, is maintained for a period of time such that the total composition contains less than about 1.0 weight percent of unreacted diphenylamine and more preferably less than about 0.8 weight percent, preferably from less than about 0.8 to about 0.2 weight percent in the product.

The reaction pressure can range up to about 250 psi or higher, preferably below about 250 psi, and more preferably in the range of about 25 to 100 psi. Inert gas, such as nitrogen, can be used to minimize oxidation of products during reaction, but mostly to allow operation at higher temperatures with the lower boiling oligomers. A nitrogen or other inert gas atmosphere, in contrast to air, suppresses the formation of products that deactivate the clay catalyst. Other benefits of nitrogen pressure include higher rates of reaction, shorter reaction times, and enhanced formation of dialkylated DPA, and may impact the trialkylated DPA. The latter may be achieved by preventing the loss of volatiles to the atmosphere.

In practice it is difficult to take the reaction to the extinction of DPA because as the reaction continues the concentration of reactants diminishes and the rates become very slow. Generally in the process of the present invention, less than 1%, and more typically less than 0.8% DPA, is left unreacted in the product mixture. If desired, lower residual amounts of diphenylamine can be obtained by continued stripping or, alternatively, by secondary treatment with a more reactive olefin such as isobutylene or styrene. Preferably, the nonene should be incrementally added to the reaction mixture to control and maintain the desired reaction temperature and to minimize premature isomerization to non-reactive olefins. However, depending on the desired product mixture it may be beneficial to add nonene to the reaction mixture all at once at a lower temperature than the reaction temperature.

Reaction time is a very flexible reaction parameter and is dependent on the reaction temperature, mole ratio of reactants and catalysts and pressure. Generally, the reaction will be carried out over a period of about 2 to 30 or more hours, preferably over a period of about 5 to 24 hours, and more preferably over a period of about 6 to 20 hours.

Upon completion of the reaction, the desired alkylated diphenylamine products can be isolated using conventional techniques, such as stripping under vacuum or separation by elution with hexane using column chromatography. Depending upon the particular reaction conditions selected the amount of monoalkylated DPA to dialkylated DPA to trialkylated DPA in the product mixture can typically range: from about 15 to about 25 weight % for the monoalkylate; from about 65 to about 75 weight % for the dialkylate; from about 7 to about 10 weight % for the trialkylate. However, under certain conditions the product mixture can be either predominantly monoalkylate or predominantly dialkylate.

EXAMPLES

The following examples are presented to illustrate certain embodiments of this invention and are not to be construed as limiting the scope of the invention.

Example 1

Runs 1.1 to 1.7

The reaction is performed in a jacketed SS 2-liter batch autoclave set-up made by Buchi AG, Switzerland (Model Bep 280). The mixing is provided by a pitched blade impeller running at 325 rpm. The impeller is driven by a magnet stirred drive. The temperature is controlled by a Julabo 12 circulating hot oil system, from Julabo Labortechnik GmbH, Germany. Temperatures and pressures are monitored using a Siemens AG, Germany Simatic™ T1505/545 PLC interfaced to a PC with Wonderware Factory Suite from Wonderware, Calif.

After being purged several times with nitrogen, the autoclave is filled with 251.6 g of DPA (Aldrich 99%+), 752.5 g of nonene (ExxonMobil, nonene/DPA molar ratio of 4.03) and 50.3 g of BASF F-24 (20% of DPA charge). The F-24 catalyst was previously dried at 150° C. in an oven under vacuum and nitrogen purge. The autoclave was purged again several times with nitrogen. The autoclave was then closed. The autoclave was heated and held at 180° C. for 10 hours. Then the autoclave was cooled and held at 150° C. for an extra 10 hours. The pressure during reaction went to a maximum of 38.1 psig. At the end of the holding periods, the autoclave was cooled to 20-65° C. and the crude product dropped out using the autoclave bottom valve. The crude was weighed and filtered using a Buchner filter to remove the F-24 catalyst, The unreacted nonene was then stripped using a rotary evaporator at 160-165° C. at 0-50 mmHg. The filtered crude, filtered stripped crude, and stripped overhead were analyzed by Gas Chromatograph "GC" as set-up below.

| | |
|---|---|
| Gas Chromatograph | Aligent 6890N with 7683 Series Injector |
| Injection Method | Direct injection "on column" |
| Injection Volume | 1 microliter |
| Column | Aligent HP-5 1091J-211 length 15 m, |
| | Nominal diameter: 320 micrometer |
| Stationary Phase | 5% Phenyl Methyl Siloxane Film thickness: |
| | 1 micrometer |
| Detector | FID |
| Integrator | Attenuation: 0 |
| Carrier gases | Helium; 4.0 ml/min, Hydrogen flow: 30 ml/min, |
| | Air flow 400 ml/min, Nitrogen 25 ml/min |
| Temperature | Injector 250 C. |
| | Oven: 1) Initial temp: 50 C., 2 min |
| | 2) Ramps: 10 C./min up to 300 C. |
| | 3) Hold: 5 min at 300 C. |
| Measuring period | 32 minutes |

The filtered crude contained 39.9 wt % unreacted nonene. The stripped overhead contained over 99.5 wt % nonene. The stripped overhead was saved for recycle in the next batch. The filtered stripped crude was a light amber liquid. It contains 0.2 wt % nonene, 0.8 wt % nonene dimer, 0.3 wt % DPA, 0.2 wt % C3-C8-DPA, 15.9 wt % mono-nonyldiphenylamine, 74.6 wt % di-nonyldiphenylamine and 8 wt % tri-nonyldiphenylamine. The reaction conditions and results are presented in Table 1.

Run 1.2 (First Recycle):

The reaction was performed under same conditions as Run 1.1 but nonene was coming from two sources: all the stripped overhead from example 1 (346.4 g) and, fresh nonene to bring the charge to a nonene/DPA mole ratio of 4 (404 g). The product contained 0.4 wt % DPA and 8.4 wt % tri-alkylated DPA.

Runs 1.3-1.7 (Second to Sixth Recycle):

The reaction was performed under same conditions as Run 1.2 but using stripped nonene from the previous example. The product of these runs contained unreacted DPA below 0.8 wt % and tri-alkylated higher than 7.4 wt %

TABLE 1

Conditions and results for Example 1

| Run Conditions | EXAMPLE 1 Run # | | | | | | |
|---|---|---|---|---|---|---|---|
| | 1.1 | 1.2 | 1.3 | 1.4 | 1.5 | 1.6 | 1.7 |
| Nonene | XOM | XOM | XOM | XOM | XOM | XOM | XOM |
| S/S# | 4146 | 4146 | 4146 | 4146 | 4246 | 4246 | 4246 |
| DPA | Aldrich 99+ | Aldrich 99+ | Aldrich 99+ | Aldrich 99+ | Aldrich 99+ | Aldrich 99+ | Aldrich 99+ |
| Nonene/DPA Mole Ratio | 4 | 4 | 4 | 4 | 4 | 4 | 4 |
| Catalyst | F-24 (Dried 150 C.) | F-24 (Dried 150 C.) | F-24 (Dried 150 C.) | F-24 (Dried 150 C.) | F-24 (Dried 150 C.) | F-24 (Dried 150 C.) | F-24 (Dried 150 C.) |
| Catalyst (wt % of DPA) | 20% | 20% | 20% | 20% | 20% | 20% | 20% |
| Temperature 1 (° C.) | 180 + 150 | 180 | 180 | 180 | 180 | 180 | 180 |
| Reaction Time 1 (h) | 20 | 10 | 10 | 10 | 10 | 10 | 10 |
| Temperature 2 (° C.) | 0 | 150 | 150 | 150 | 150 | 150 | 150 |
| Reaction Time 2 (h) | 0 | 10 | 10 | 10 | 10 | 10 | 10 |
| Recycle # | 0 | 1 | 2 | 3 | 4 | 5 | 6 |
| Recycle Overhead Run # | 0 | 1.1 | 1.2 | 1.3 | 1.4 | 1.5 | 1.6 |
| Recycle Catalyst # | 0 | 0 | 0 | 0 | 0 | 0 | 0 |
| Recycle Catalyst Run # | 0 | 0 | 0 | 0 | 0 | 0 | 0 |
| Note | | Recycle 1 (Run 1.1) | Recycle 2 (Run 1.2) | Recycle 3 (Run 1.3) | Recycle 4 (Run 1.4) | Recycle 5 (Run 1.5) | Recycle 6 (Run 1.6) |
| Nonene[1] | 0.2 | 0.2 | 0.4 | 0.3 | 0.2 | 0.2 | 0.5 |
| Nonene Dimer[1] | 0.8 | 0.8 | 0.7 | 0.8 | 1.0 | 0.7 | 0.8 |
| DPA[1] | 0.3 | 0.4 | 0.4 | 0.5 | 0.6 | 0.5 | 0.6 |
| $C_3$-$C_8$DPA[1] | 0.2 | 0.4 | 0.3 | 0.3 | 0.5 | 0.3 | 0.4 |
| $C_9$DPA[1] | 15.9 | 19.7 | 18.4 | 19. | 21.7 | 19.9 | 21.2 |
| Di$C_9$DPA[1] | 74.6 | 70.1 | 70.1 | 70.8 | 66.7 | 70.8 | 69.1 |
| Tri$C_9$DPA[1] | 8.0 | 8.4 | 9.6 | 8.3 | 9.3 | 7.5 | 7.4 |
| Others[1] | 0.0 | 0.0 | 0.0 | 0.0 | 0.0 | 0.0 | 0.0 |
| Calculated N wt % | 3.5 | 3.5 | 3.5 | 3.5 | 3.6 | 3.6 | 3.6 |
| DPA(g) | 251.6 | 251.3 | 251.3 | 251.4 | 252.3 | 255.0 | 251.5 |
| Make-up Nonene (g) | 752.5 | 404.0 | 386.7 | 382.5 | 358.0 | 397.0 | 374.3 |
| Recycle Nonene (g) | 0.0 | 346.4 | 364.0 | 368.6 | 395.8 | 367.1 | 377.4 |
| Catalyst (g) | 50.3 | 50.3 | 50.3 | 50.3 | 50.5 | 51.0 | 50.3 |
| Crude Product (g) | 899.5 | 909.1 | 914.8 | 900.6 | 914.0 | 927.7 | 924.0 |
| Stripped Product (g) | 546.9 | 540.2 | 542.7 | 536.2 | 539.6 | 545.7 | 533.5 |
| % Unreacted Nonene in filtered crude | 39.2 | 40.6 | 40.7 | 40.5 | 41.0 | 41.2 | 42.3 |

[1] wt % component based upon total composition

Example 2

Runs 2.1 to 2.3

The conditions and procedures primarily as set forth in Example 1 were repeated with the parameters and results set forth in Table 2, below. The reaction time was set at a first reaction temperature of 180° C. for about 5 hours and thereafter reduced to 150° C. for about 5 hours. Unreacted DPA in the product content moved consecutively from 0.4, 0.7 to 0.9 wt %. The particulars for Example 2 are depicted in Table 2, below.

TABLE 2

| Run Conditions | EXAMPLE 2 Run # | | |
|---|---|---|---|
| | 2.1 | 2.2 | 2.3 |
| Nonene | XOM | XOM | XOM |
| S/S# | 4246 | 4246 | 4246 |
| DPA | Aldrich 99+ | Aldrich 99+ | Aldrich 99+ |
| Nonene/DPA Mole Ratio | 4 | 4 | 4 |
| Catalyst | F-24 (Dried 150 C.) | F-24 (Dried 150 C.) | F-24 (Dried 150 C.) |
| Catalyst (wt % of DPA) | 20% | 20% | 20% |
| Temperature 1 (° C.) | 180 | 180 | 180 |
| Reaction Time 1 (h) | 5 | 5 | 5 |
| Temperature 2 (° C.) | 150 | 150 | 150 |
| Reaction Time 2 (h) | 5 | 5 | 5 |
| Recycle # | 0 | 1 | 2 |
| Recycle Overhead Run # | 0 | 2.1 | 2.2 |
| Recycle Catalyst # | 0 | 0 | 0 |
| Recycle Catalyst Run # | 0 | 0 | 0 |
| Note | | Recycle 1 (Run 2.1) | Recycle 2 (Run 2.2) |
| Nonene[1] | 0.1 | 0.0 | 0.1 |
| Nonene Dimer[1] | 0.6 | 0.7 | 0.4 |
| DPA[1] | 0.4 | 0.7 | 0.9 |
| $C_3$-$C_8$DPA[1] | 0.2 | 0.7 | 0.4 |
| $C_9$DPA[1] | 21.0 | 25.5 | 27.8 |
| Di$C_9$DPA[1] | 71.5 | 67.3 | 65.6 |
| Tri$C_9$DPA[1] | 6.2 | 5.1 | 4.8 |
| Others[1] | 0.0 | 0.0 | 0.0 |
| Calculated N wt % | 3.6 | 3.7 | 3.7 |
| DPA (g) | 251.5 | 251.3 | 250.8 |
| Make-up Nonene (g) | 751.0 | 379.1 | 370.3 |
| Recycle Nonene (g) | 0.0 | 372.0 | 380.9 |
| Catalyst (g) | 50.3 | 50.3 | 50.2 |
| Crude Product (g) | 918.9 | 907.7 | 918.9 |

TABLE 2-continued

| | EXAMPLE 2 Run # | | |
|---|---|---|---|
| Run Conditions | 2.1 | 2.2 | 2.3 |
| Stripped Product (g) | 535.2 | 522.4 | 513.4 |
| % Unreacted Nonene in filtered crude | 41.8 | 42.4 | 44.1 |

[1]wt % component based upon total composition

Example 3

Runs 3.1 to 3.3

Following the procedures set forth in Example 2 the conditions and results are set forth in Table 3. In Example 3 the first higher temperature was again about 180° C. for about 5 hours but the reduced temperature of about 150° C. was held for about 10 hours. The unreacted DPA content in the product was 0.3 wt %, 0.3 wt % and 0.6 wt %, respectively for the runs. The particulars for Example 3 are depicted in Table 3, below.

TABLE 3

| | EXAMPLE 3 Run # | | |
|---|---|---|---|
| Run Conditions | 3.1 | 3.2 | 3.3 |
| Nonene | XOM | XOM | XOM |
| S/S# | 4246 | 4246 | 4246 |
| DPA | Aldrich 99+ | Aldrich 99+ | Aldrich 99+ |
| Nonene/DPA Mole Ratio | 4 | 4 | 4 |
| Catalyst | F-24 (Dried 150 C.) | F-24 (Dried 150 C.) | F-24 (Dried 150 C.) |
| Catalyst (wt % of DPA) | 20% | 20% | 20% |
| Temperature 1 (° C.) | 180 | 180 | 180 |
| Reaction Time 1 (h) | 5 | 5 | 5 |

TABLE 3-continued

| | EXAMPLE 3 Run # | | |
|---|---|---|---|
| Run Conditions | 3.1 | 3.2 | 3.3 |
| Temperature 2 (° C.) | 150 | 150 | 150 |
| Reaction Time 2 (h) | 10 | 10 | 10 |
| Recycle # | 0 | 1 | 2 |
| Recycle Overhead Run # | 0 | 3.1 | 3.2 |
| Recycle Catalyst # | 0 | 0 | 0 |
| Recycle Catalyst Run # | 0 | 0 | 0 |
| Note | | Recycle 1 (Run 3.1) | Recycle 2 (Run 3.2) |
| Nonene[1] | 0.1 | 0.1 | 0.1 |
| Nonene Dimer[1] | 0.6 | 0.6 | 0.5 |
| DPA[1] | 0.3 | 0.3 | 0.6 |
| C3-C8DPA[1] | 0.2 | 0.2 | 0.3 |
| C9DPA[1] | 17.1 | 17.1 | 20.9 |
| DiC9DPA[1] | 75.1 | 75.1 | 70.1 |
| TriC9DPA[1] | 6.5 | 6.5 | 7.6 |
| Others[1] | 0.0 | 0.0 | 0.0 |
| Calculated N wt % | 3.5 | 3.5 | 3.6 |
| DPA (g) | 251.3 | 250.8 | 251.0 |
| Make-up Nonene (g) | 751.0 | 385.0 | 373.1 |
| Recycle Nonene (g) | 0.0 | 364.1 | 376.8 |
| Catalyst (g) | 50.3 | 50.2 | 50.2 |
| Crude Product (g) | — | 915.0 | 907.1 |
| Stripped Product (g) | — | 534.1 | 538.7 |
| % Unreacted Nonene in filtered crude | 40.1 | 41.6 | 40.6 |

[1]wt % component based upon total composition

Comparative Example A

Runs A.1-A.5

This comparative example was performed in a similar fashion as Example 1, but at a reaction temperature of 150° C. for 20 hours, instead of a two distinct temperatures (180° C./10 hours and 150/10 hours). The DPA content of the product moved from 0.3 to 1.2 wt %. The particulars for Comparative Example A are depicted in Table 4, below.

TABLE 4

| | COMPARATIVE EXAMPLE A RECYCLE LOW TEMPERATURE Run # | | | | |
|---|---|---|---|---|---|
| Run Conditions | A.1 | A.2 | A.3 | A.4 | A.5 |
| Nonene | XOM | XOM | XOM | XOM | XOM |
| S/S# | 4146 | 4146 | 4146 | 4146 | 4246 |
| DPA | Aldrich 99+ | Aldrich 99+ | Aldrich 99+ | Aldrich 99+ | Aldrich 99+ |
| Nonene/DPA Mole Ratio | 4 | 4 | 4 | 4 | 4 |
| Catalyst | F-24 (Dried 150 C.) | F-24 (Dried 150 C.) | F-24 (Dried 150 C.) | F-24 (Dried 150 C.) | F-24 (Dried 150 C.) |
| Catalyst (wt % of DPA) | 20% | 20% | 20% | 20% | 20% |
| Temperature 1 (° C.) | 150 | 150 | 150 | 150 | 150 |
| Reaction Time 1 (h) | 20 | 20 | 20 | 20 | 20 |
| Temperature 2 (° C.) | 0 | 0 | 0 | 0 | 0 |
| Reaction Time 2 (h) | 0 | 0 | 0 | 0 | 0 |
| Recycle # | 0 | 1 | 2 | 3 | 4 |
| Recycle Overhead Run # | 0 | A.1 | A.2 | A.3 | A.4 |
| Recycle Catalyst # | 0 | 0 | 0 | 0 | 0 |
| Recycle Catalyst Run # | 0 | 0 | 0 | 0 | 0 |
| Note | | Recycle 1 (Run A.1) | Recycle 2 (Run A.2) | Recycle 3 (Run A.3) | Recycle 4 (Run A.4) |
| Nonene[1] | 0.5 | 0.1 | 0.1 | 0.1 | 0.0 |
| Nonene Dimer[1] | 0.4 | 0.3 | 0.2 | 0.2 | 0.2 |
| DPA[1] | 0.3 | 0.8 | 0.8 | 1.2 | 1.2 |
| C3-C8DPA[1] | 0.1 | 0.2 | 0.1 | 0.3 | 0.2 |
| C9DPA[1] | 16.7 | 23.3 | 25.8 | 32.3 | 31.7 |
| DiC9DPA[1] | 77.2 | 70.6 | 68.7 | 63.0 | 63.4 |
| TriC9DPA[1] | 4.8 | 4.7 | 4.4 | 2.9 | 3.2 |
| Others[1] | 0.0 | 0.0 | 0.0 | 0.0 | 0.0 |

TABLE 4-continued

| | COMPARATIVE EXAMPLE A RECYCLE LOW TEMPERATURE Run # | | | | |
|---|---|---|---|---|---|
| Run Conditions | A.1 | A.2 | A.3 | A.4 | A.5 |
| Calculated N wt % | 3.5 | 3.6 | 3.7 | 3.8 | 3.8 |
| DPA (g) | 251.0 | 251.3 | 251.4 | 251.5 | 251.6 |
| Make-up Nonene (g) | 750.6 | 383.5 | 390.0 | 398.4 | 338.8 |
| Recycle Nonene (g) | 0.0 | 368.2 | 363.0 | 356.0 | 413.0 |
| Catalyst (g) | 50.2 | 50.3 | 50.3 | 50.3 | 50.3 |
| Crude Product (g) | | 895.9 | 929.0 | 922.4 | 915.2 |
| Stripped Product (g) | | 528.8 | 520.2 | 503.6 | 504.2 |
| % Unreacted Nonene in filtered crude | 40.6 | 41.0 | 44.0 | 45.4 | 44.9 |

[1] wt % component based upon total composition

Comparative Example B

Runs B.1-B.3

The comparative example was performed similar to Comparative Example A but the reaction temperature was maintained at 180° C./20 hours and 10 wt % catalyst. DPA content moved consecutively from 0.8, 1.2 and 1.3. The particulars for Comparative Example B are depicted in Table 5, below.

TABLE 5

| | COMPARATIVE EXAMPLE B HIGH TEMPERATURE Run # | | |
|---|---|---|---|
| Run Conditions | B.1 | B.2 | B.3 |
| Nonene | XOM | XOM | XOM |
| S/S# | 4146 | 4146 | 4146 |
| DPA | Aldrich 99+ | Aldrich 99+ | Aldrich 99+ |
| Nonene/DPA Mole Ratio | 5 | 5 | 5 |
| Catalyst | F-24 (Dried 150 C.) | F-24 (Dried 150 C.) | F-24 (Dried 150 C.) |
| Catalyst (wt % of DPA) | 10% | 10% | 10% |
| Temperature 1 (° C.) | 180 | 180 | 180 |
| Reaction Time 1 (h) | 20 | 20 | 20 |
| Temperature 2 (° C.) | 0 | 0 | 0 |
| Reaction Time 2 (h) | 0 | 0 | 0 |
| Recycle # | 0 | 1 | 2 |
| Recycle Overhead Run # | 0 | B.1 | B.2 |
| Recycle Catalyst # | 0 | 0 | 0 |
| Recycle Catalyst Run # | 0 | 0 | 0 |
| Note | Recycle Start | Recycle 1 (Run B.1) | Recycle 2 (Run B.2) |
| Nonene[1] | 0.1 | 0.12 | 0.17 |
| Nonene Dimer[1] | 0.9 | 1.1 | 1.3 |
| DPA[1] | 0.8 | 1.1 | 1.3 |
| $C_3$-$C_8$DPA[1] | 0.3 | 0.5 | 0.4 |
| $C_9$DPA[1] | 19.3 | 21.5 | 23.3 |
| Di$C_9$DPA[1] | 71.4 | 68.8 | 66.5 |
| Tri$C_9$DPA[1] | 7.2 | 7.0 | 6.9 |
| Others[1] | 0.0 | 0.0 | 0.0 |
| Calculated N wt % | 3.6 | 3.6 | 3.6 |
| DPA (g) | 226.4 | 232.1 | 225.7 |
| Make-up Nonene (g) | 847.0 | 380.7 | 329.0 |
| Recycle Nonene (g) | 0.0 | 487.3 | 513.8 |
| Catalyst (g) | 22.6 | 23.2 | 22.6 |
| % Unreacted Nonene in filtered crude | 49.7 | 50.5 | 51.2 |

[1] wt % component based upon total composition

Comparative Example C

Runs C.1-C.2

This comparative example was performed in a similar fashion as Example 1, but nonene/DPA molar ratio of 3. DPA moved from 0.3 to 1.0. The particulars for Comparative Example C are depicted in Table 6, below.

TABLE 6

| | COMPARATIVE C CHARGE MOLE RATIO Run # | |
|---|---|---|
| Run Conditions | C.1 | C.2 |
| Nonene | XOM | XOM |
| S/S# | 4246 | 4246 |
| DPA | Aldrich 99+ | Aldrich 99+ |
| Nonene/DPA Mole Ratio | 3 | 3 |
| Catalyst | F-24 (Dried 150 C.) | F-24 (Dried 150 C.) |
| Catalyst (wt % of DPA) | 20% | 20% |
| Temperature 1 (° C.) | 180 | 180 |
| Reaction Time 1 (h) | 10 | 10 |
| Temperature 2 (° C.) | 150 | 150 |
| Reaction Time 2 (h) | 10 | 10 |
| Recycle # | 0 | 1 |
| Recycle Overhead Run # | 0 | C.1 |
| Recycle Catalyst # | 0 | 0 |
| Recycle Catalyst Run # | 0 | 0 |
| Note | | Recycle 1 (Run C.1) |
| Nonene[1] | 0.1 | 30.4 |
| Nonene Dimer[1] | 0.4 | 0.4 |
| DPA[1] | 0.6 | 1.0 |
| $C_3$-$C_8$DPA[1] | 0.3 | 0.3 |
| $C_9$DPA[1] | 21.3 | 18.9 |
| Di$C_9$DPA[1] | 69.7 | 44.7 |
| Tri$C_9$DPA[1] | 7.6 | 4.4 |
| Others[1] | 0.0 | 0.0 |
| Calculated N wt % | 3.6 | 2.6 |
| DPA (g) | 325.8 | 326.5 |
| Make-up Nonene (g) | 732.0 | 460.2 |
| Recycle Nonene (g) | 0.0 | 271.9 |
| Catalyst (g) | 65.0 | 65.3 |
| Crude Product (g) | 953.2 | 948.5 |
| Stripped Product (g) | 674.6 | 665.4 |
| % Unreacted Nonene in filtered crude | 29.2 | 29.8 |

[1] wt % component based upon total composition

Comparative Example D

This comparative example was performed in a similar fashion as Example 1, but instead of using a first high temperature followed by a reduced second temperature; this example used a low temperature and then a high temperature. Thus the conditions are largely the same as in Example 1, but using a first low temperature of 150° C./10 hours and a second higher temperature of 180° C./10 hour. DPA content is 1.2 wt %. Recycle was not attempted due to the unsatisfactory DPA content.

|  | COMPARATIVE EXAMPLE D |
|---|---|
| Run Conditions | Run # D.1 |
| Nonene | XOM |
| S/S# | 4246 |
| DPA | Aldrich 99+ |
| Nonene/DPA Mole Ratio | 4 |
| Catalyst | F-24 (Dried 150 C.) |
| Catalyst (wt % of DPA) | 20% |
| Temperature 1 (° C.) | 150 |
| Reaction Time 1 (h) | 10 |
| Temperature 2 (° C.) | 180 |
| Reaction Time 2 (h) | 10 |
| Recycle # | 0 |
| Recycle Overhead Run # | 0 |
| Recycle Catalyst # | 0 |
| Recycle Catalyst Run # | 0 |
| Note |  |
| Nonene[1] | 0.1 |
| Nonene Dimer[1] | 0.9 |
| DPA[1] | 1.2 |
| $C_3$-$C_8$DPA[1] | 0.3 |
| $C_9$DPA[1] | 21.2 |
| Di$C_9$DPA[1] | 67.2 |
| Tri$C_9$DPA[1] | 9.0 |
| Others[1] | 0.0 |
| Calculated N wt % | 3.6 |
| DPA | 250.8 |
| Make-up Nonene | 750.0 |
| Recycle Nonene | 0.0 |
| Catalyst | 50.2 |
| Crude Product | 908.3 |
| Stripped Product | 532.0 |
| % Unreacted Nonene in filtered crude | 41.4 |

[1] wt % component based upon total composition

What is claimed is:

1. A process for preparing an alkylated diphenylamine product using consecutive recycle of recovered nonene, said process comprising:
   a) recovering residual nonene from an acid clay catalyzed alkylation reaction of nonene with diphenylamine:
   b) charging diphenylamine and recovered residual nonene from step a) with nonene or isomeric nonene to a reactor with an acid clay catalyst; wherein the charge mole ratio of diphenylamine to total nonene is from about 1:4 to 1:6;
   c) heating the reactor to a first temperature of from about 175° C. to about 200° C. in the presence of the acid clay catalyst under reactive conditions for a suitable period of time to alkylate a majority of charged diphenylamine;
   d) reducing the reaction temperature to a second temperature of from about 140° C. to about 160° C. for a suitable period of time such that the total composition contains less than about 1 wt % of unreacted diphenylamine; and
   e) repeating steps a) through d) three or more times; and further comprising recovering the alkylated diphenylamine product from the reactor, wherein the nonylated diphenylamine product is characterized by having from about 15 to about 30 weight % of the monoalkylate; from about 65 to about 75 weight % of the dialkylate; and from about 5 to about 10 weight % of the trialkylate; and wherein the process is conducted substantially free of halogens.

2. The process of claim 1, wherein the recovered residual nonene is from about 25 to about 60 mole percent of the total nonene charged to the reactor.

3. The process of claim 2, wherein the recovered residual nonene is from about 40 to about 60 mole percent of the total nonene charged to the reactor.

4. The process of claim 1, wherein in step b. the charge mole ratio of diphenylamine to total nonene is about 1:4.

5. The process of claim 1, wherein in step c) the first temperature is from about 180° C. to about 195° C.

6. The process of claim 5, wherein the catalyst is present in an amount of 5 to 20 weight percent based upon the weight of diphenylamine.

7. The process of claim 6, wherein the catalyst is present in an amount of 10 weight percent or greater.

8. The process of claim 7, wherein the catalyst of step c) is the same type of catalyst employed in step a).

9. The process of claim 6, wherein the catalyst is a powder grade, acid activated montmorillonite clay.

10. The process of claim 9, wherein the powder grade catalyst has an average particle size of about 30 microns.

11. The process of claim 6, further comprising thermally treating the catalyst prior to use.

12. The process of claim 11, wherein the thermal treatment removes substantially all of the freely associated water from the catalyst.

13. The process of claim 11, wherein the catalyst is regenerable.

14. An alkylated diphenylamine product prepared according to the process of claim 1.

15. The product prepared according to claim 14, wherein the alkylated diphenylamine product is characterized by having from about 15 to about 25 weight % of the mononyldiphenylamine; from about 65 to about 75 weight % of the dinonyldiphenylamine; and from greater than about 7 to about 10 weight % of the trinonyldiphenylamine.

16. The product prepared according to claim 15, wherein the trinonyldphenylamuic content is greater than about 8 weight %.

17. A lubricating oil composition comprising a major amount of an oil of lubricating viscosity and a minor amount of the product prepared according to claim 14.

* * * * *